United States Patent [19]

Weitemeyer et al.

[11] Patent Number: 5,354,906
[45] Date of Patent: Oct. 11, 1994

[54] AQUEOUS LIQUID SOLUTION OF A BETAINE WITH A SOLIDS CONTENT OF AT LEAST 40% BY WEIGHT

[75] Inventors: Christian Weitemeyer, Essen; Willi Foitzik, Bottrop; Hans-Dieter Käseborn; Burghard Grüning, both of Essen; Uwe Begoihn, Bochum, all of Netherlands

[73] Assignee: Th. Goldschmidt AG, Essen, Fed. Rep. of Germany

[21] Appl. No.: 16,917

[22] Filed: Feb. 12, 1993

[30] Foreign Application Priority Data

Mar. 9, 1992 [DE] Fed. Rep. of Germany ....... 4207386

[51] Int. Cl.$^5$ ............................................. C07C 233/00
[52] U.S. Cl. ........................................ 554/52; 554/68; 554/69; 252/544; 252/546
[58] Field of Search ................. 252/546, 547, DIG. 5, 252/DIG. 7, DIG. 13, DIG. 14; 554/52, 68, 69

[56] References Cited

U.S. PATENT DOCUMENTS 4,243,549  1/1981  Messenger et al. ................ 252/355
4,861,517  8/1984  Bade .................................. 252/546

OTHER PUBLICATIONS

Anthony L. L. Hunting, "Shampoo Thickeners" Mar. 1982, pp. 53–63.

*Primary Examiner*—José G. Dees
*Assistant Examiner*—Deborah D. Carr
*Attorney, Agent, or Firm*—Anderson Kill Olick & Oshinsky

[57] ABSTRACT

An aqueous liquid solution of a betaine of the following general formula is disclosed

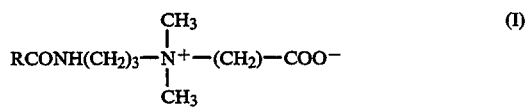

in which R is an alkyl group of coconut fatty acids, preferably hydrogenated coconut fatty acids, or a fatty acid mixture which, on the average, corresponds to coconut fatty acids, wherein the solution has a solids content of at least 40% by weight, a pH of 5 to 8 and an aminoamide content of not more than 1% by weight, characterized by a content of 1 to 3% by weight, based on the solution, of one or more saturated fatty acids with, on the average, 8 to 18 carbon atoms or one or more unsaturated fatty acids with, on the average, 8 to 24 carbon atoms and 0 to 4% by weight of glycerin, based on the solution.

10 Claims, No Drawings

AQUEOUS LIQUID SOLUTION OF A BETAINE WITH A SOLIDS CONTENT OF AT LEAST 40% BY WEIGHT

BACKGROUND OF THE INVENTION

The invention relates to an aqueous liquid solution of a betaine of the general formula

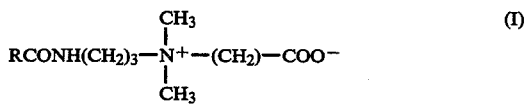

in which R is an alkyl group of coconut fatty acids, preferably hydrogenated, or a fatty acid mixture which, on the average, corresponds to coconut fatty acids, the solution having a solids content of at least 40% by weight, a pH of 5 to 8 and an aminoamide content of not more than 1% by weight.

More particularly, the invention relates to aqueous liquid solutions of a betaine of the aforementioned type with a solids content of at least 42% by weight and particularly of at least 45% by weight. The solids content is defined as the weight which is determined by evaporating sample on a flat glass disk for 2 hours at 105° C.

It is well known that solutions of betaines of the aforementioned type are liquid only below a particular concentration of total solids, which depends on the fatty acids or fatty acid mixtures used for their preparation. For example, a solution of a betaine derived from coconut fatty acids solidifies at a solids content of about 40% by weight. For this reason, conventional, commercial, aqueous solutions of coconut amidopropylbetaine, derived from coconut fat, have total solids concentrations which are clearly below 40% by weight and in most cases about 35% by weight. The maximum achievable concentration of a still flowable solution of a betaine decreases as the number of carbon atoms is increased. If the fatty acid mixture contains a higher proportion of unsaturated fatty acids, the concentrations achievable frequently are comparatively higher than those achievable with saturated fatty acids.

A conventional commercial betaine solution typically has the following composition:

| | | |
|---|---|---|
| water: | 64% by weight | |
| betaine: | 30% by weight | |
| NaCl: | 5% by weight | ca. 36% by weight total solids |
| glycerin: | 0.3% by weight | |
| fatty acid: | 0.5% by weight | |
| aminoamide: | ca.0.3% by weight | |

In this sense, the solids content represents the sum of the components other than water. The proportions of betaine and sodium chloride arise out of the stoichiometry of the reaction of the fatty amide with tertiary amino groups (aminoamide) and sodium chloroacetate according to:

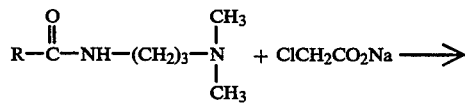

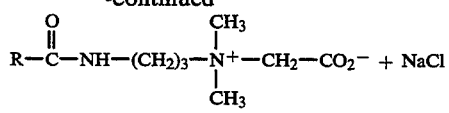

A small amount of aminoamide normally remains in the product because the reaction is incomplete. This proportion can, however, be reduced further by an adapted stoichiometry and reaction procedure. The further typical components listed originate from the synthesis of the aminoamide. If the aminoamide has been obtained by the reaction of the fatty acids with 3-N,N-dimethylaminopropylamine, residual amounts of fatty acids are still present. If the aminoamide has been synthesized from fats and 3-N,N-dimethylaminopropylamine, portions of fatty acids as well as glycerin are present.

The aminoamide, if anything, is unwanted for physiological reasons and therefore every effort is made to keep the content thereof low. On the other hand, glycerin and fatty acids are desirably used and frequently in cosmetic preparations. In the case of glycerin, primarily skin care products prepared therewith are esteemed. Fatty acids have good effects on formulations. For example, A. L. Hunting describes the use of fatty acids as thickening agents in shampoo formulations in "Cosmetics and Toiletries" 97, 53 (1982). Particularly in the form of their salts, an increase in viscosity is brought about by their use.

There has been no lack of attempts to produce betaine solutions of higher concentration. However, such attempts have been successful only if extraneous compounds are used or special methods are employed, which increase the cost of the product.

For example, in U.S. Pat. No. 4,243,549, pourable aqueous preparations are described which contain, for example, 33.5% by weight of a betaine, 33.5% by weight of an ethoxylated sodium alkyl sulfate, 9% by weight of sodium chloride and 2 to 3% by weight of impurities, the remainder being water. These mixtures exist in the form of the so-called G phase. The flowability of such mixtures is based on the special micellar structure of the G phase, which exists only within a relatively narrow concentration range. However, the required presence of equal amounts by weight of anionic surfactants is undesirable for many formulations in which betaine solutions are used. Even if anionic surfactants are added for a later application, the user himself wants to determine which anionic surfactants are used. Mixtures with cationic surfactants are not possible, because such surfactants interact with anionic surfactants.

German patent 36 13 944 relates to a method for the preparation of flowable and pumpable solutions containing at least 70% by weight of betaine. For the synthesis of the betaine,
a) the ammonium salt of the halogenated carboxylated acid is used as salt,
b) the quaternization is carried out in a polar organic solvent, which may not contain more than 20% by weight of water,
c) after the quaternization, any water contained is distilled off azeotropically and the precipitated ammonium halide is removed, after which
d) the solvent is distilled off partly or completely and
e) before, at the same time as or after the distillation, the concentration of the betaine in the solvent or solvent mixture desired for the application is adjusted to the desired value.

The need to use solvents and to remove the precipitated ammonium chloride, for example, by filtration, has proven to be a disadvantage of this method. Moreover, the addition of preferably aliphatic diols in amounts of 2 to 15% by weight based on the solution, and of 0.5 to 10% by weight of ethanol was recommended in order to attain the desired, low viscosity. The diol and/or ethanol content is also not always desirable and tolerable.

The object of German patent 37 26 322 is a method for the synthesis of the above-named betaines in the form of concentrated, aqueous solutions. The concentration of the preferably still hot solution obtained after the quaternization is adjusted to the desired value, if necessary, by evaporation of water, and mineral acid is added to the solution and, before or after the concentration is adjusted to the desired value, mineral acid is added to the solution in such amounts that the pH of the solution is 1 to 4.5. However, corrosion problems, which make the use of acid resistant material necessary for storage tanks, tank cars, etc., arise during the storage, transport and use of the acidic betaine solutions.

Finally, reference is made to the German patent 38 26 654, according to which concentrated betaine solutions are obtained owing to the fact that: nonionic, water soluble surfactants are added to the reaction mixture before or after the quaternization reaction or to the solution of betaine obtained in such amounts; the finished solution contains 3 to 20% by weight of nonionic surfactants and an adjustment of the pH of the solution by the addition of alkaline solution to a pH of $\geq 5$ to 9 is precluded after the quaternization. In this case also, the betaine solution contains an extraneous, nonionic surfactant, the presence of which can be undesirable during the later use of the betaine solution.

SUMMARY OF THE INVENTION

An object of the present invention is to provide aqueous, liquid betaine solutions with a total solids content of at least 40% by weight, preferably, of at least 42% by weight and, particularly, at least 45% by weight and a pH of 5 to 8, which are free of extraneous surfactants and organic solvents.

Another object of the invention is the provision of a method for the preparation of such liquid betaine solution for which no additional steps, such as filtrations, are required.

Still another object of the invention is the provision of such betaine solution which are free of admixtures and impurities which remain in the betaine solutions because of the incomplete reaction of the betaine solutions used, where these residual amounts are undesirable for physiological reasons, particularly the impurities monochloroacetate and fatty acid dimethylaminopropylamide ("aminoamide").

Another important object of the invention is the provision of such betaine solutions wherein the concentration thereof is such that special measures to preserve the solutions against bacterial decomposition are not required, especially betaine solutions which have a solids content of at least about 40% by weight.

Surprisingly, it has been discovered that these and other objectives are accomplished by adjusting the betaine solution so that it contains a certain amount of free fatty acid and, optionally, small amounts of glycerin.

According to the invention, an aqueous, flowing solution of a betaine of the general formula

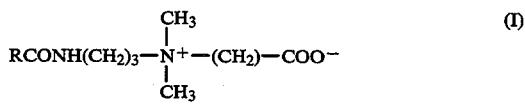

wherein R is the alkyl group of coconut fatty acid, preferably hydrogenated, or a fatty acid mixture which corresponds, on the average, to coconut fatty acids, the solution having a solids content of at least 40% by weight, a pH of 5 to 8 and an aminoamide content of not more than 1% by weight, comprises i to 3% by weight, based on the solution, of one or more saturated fatty acids having an average of 8 to 18 carbon atoms or one or more unsaturated fatty acids having an average of 8 to 24 carbon atoms and 0 to 4% by weight of glycerin, based on the solution.

DESCRIPTION OF THE INVENTION

As saturated fatty acids with, on the average, 8 to 18 carbon atoms, the naturally occurring fatty acids and fatty acid mixtures, in particular, come into consideration, fatty acids and fatty acid mixtures with, on the average 8 to 12 carbon atoms, being preferred.

As unsaturated fatty acids with, on the average, 8 to 24 carbon atoms, the naturally occurring unsaturated fatty acids and their mixtures, such as oleic acid, ricinoleic acid and the fatty acids obtained from fish oil are preferred.

Particularly preferred are hydrogenated and non-hydrogenated coconut fatty acids, lauric acid, oleic acid and ricinoleic acid.

In this connection, the fatty acid which is present in free form can correspond to the fatty acid RCOOH, from which the betaine is derived.

Preferably, the inventive betaine solution is characterized by a content of 1.5 to 3% by weight of fatty acid and I to 2% by weight of glycerin.

Those skilled in the art understand the coconut fatty acids to be a commercially offered mixture of hydrogenated or non-hydrogenated fatty acids, which are obtained from coconut oil and have the following average composition:

| Coconut Fatty Acids Number of Carbon Atoms | Non-Hydrogenated % by weight | Hydrogenated % by weight |
| --- | --- | --- |
| 6 | 0–1 | 0–1 |
| 8 | 5–10 | 5–10 |
| 10 | 3–10 | 5–10 |
| 12 | 43–53 | 43–53 |
| 14 | 15–22 | 15–22 |
| 16 | 7–14 | 7–14 |
| 18 | 2–8 | 4–12 |
| 18 monounsaturated | 2–12 | 0–1 |
| 18 disaturate | 0–3 | 0 |
| 18 triunsaturated | 0–3 | 0 |

Other fatty acids, such as ricinoleic acid or erucic acid can be contained in amounts of 0 to 3% by weight.

According to the invention, the term, coconut fatty aids, also comprises optionally hydrogenated palm kernel fatty acids.

| Palm Kernel Fatty Acids Number of Carbon Atoms | Non-Hydrogenated % by weight | Hydrogenated % by weight |
| --- | --- | --- |
| 6 | 0–1 | 0–1 |
| 8 | 3–6 | 3–6 |
| 10 | 3–6 | 3–6 |
| 12 | 40–52 | 40–52 |
| 14 | 14–18 | 14–18 |
| 16 | 6–14 | 6–14 |
| 18 | 1–8 | 10–17 |
| 18 monounsaturated | 9–16 | 0–2 |
| 18 disaturate | 1–3 | 0 |
| 18 triunsaturated | 0–1 | 0 |

In the case of betaines which are derived from fatty acids which have not been hydrogenated, the adjustment of the free fatty acid content and of the pH generally suffice for obtaining the desired, concentrated betaine solutions. If hydrogenated coconut fatty acids or palm kernel fatty acids are used, it is generally advisable to add up to 4% by weight of glycerin. The use of hydrogenated coconut fatty acids or palm kernel fatty acids is preferred.

Examples of inventive betaine solutions are:

| Type of Betaine R-COOH | Betaine | Sodium Chloride | Free Fatty Acids | Glycerin | Viscosity mPas, 25° C. |
| --- | --- | --- | --- | --- | --- |
| | | (in % by weight) | | | |
| Coconut Fatty Acids | 36.8 | 6.2 | 1.06 | 0.89 | 85 |
| Coconut Fatty Acids Hydrogenated | 36.0 | 6.6 | 1.55 | 0.94 | 75 |
| Palm Kernel Fatty Acids | 36.7 | 6.2 | 1.78 | 0 | 90 |

According to a further aspect of the invention, the inventive betaine solutions are prepared by quaternizing a compound of the general formula

(II)

wherein R is defined as above, with chloroacetic acid or a salt thereof at elevated temperature, wherein a fatty acid aminoamide of the general formula II which contains the desired amount of free fatty acid is used for the quaternization reaction or the desired amount of fatty acid is added to the reaction mixture before or during the quaternization reaction and optionally adding glycerin to the reaction mixture.

The concept of "elevated reaction temperatures" is defined generally as temperatures of 80° to 180° C. If temperatures of more than 100° C. are employed, the reactions must be carried out in a closed reactor. Temperatures of 120° to 160° C. are preferred, since the viscosity of the reaction medium is particularly low and the reaction proceeds particularly rapidly in this temperature range.

The amount of chloroacetic acid for the reaction advisably is chosen so that at the end of the reaction, the aminoamide is consumed with the exception of residues of ≦1% by weight. It is furthermore possible to reduce the aminoamide content by selecting a suitable alkaline pH, as described in the German patent 29 26 479.

Sodium chloroacetate is preferably used as the salt of monochloroacetic acid. It can also be formed in situ in the reaction mixture from chloroacetic acid and sodium hydroxide solution.

Optionally, the pH is adjusted at the end of the reaction with a suitable acid to a value of 5 to 8 before the temperature is lowered to room temperature. The pH range of 5 to 7 and especially of 5.5 to 6.5 is preferred.

If, for the preparation of the betaine solutions of the invention, an aminoamide of formula II is used which already contains the desired amount of free fatty acid, the latter will in most cases be identical with the fatty acid RCOOH of the aminoamide. The content of free fatty acid can then be taken into consideration in the formulation for the preparation of the aminoamide. It is, however, also possible to use an aminoamide which has an acid number of 0 or approximately 0 and to add to this one or more saturated fatty acids with, on the average, 8 to 24 carbon atoms.

In the event that glycerin is added, this may be done before or during the quaternization reaction. Although the addition of glycerin after the quaternization reaction is not excluded, it is not advantageous.

The betaine solutions of the invention fulfill the requirement of being free of extraneous surfactants and have an aminoamide content of 1% by weight. It is not necessary to add antimicrobial agents to these solutions. Moreover, they are liquid up to a solids content of about 48% by weight, depending on the average chain length of the fatty acid mixture used and on the degree of unsaturation of these fatty acids.

In the following examples which further illustrate the invention, the preparation of the betaine solutions of the invention is described in greater detail, it being understood that the illustrative examples are given by way of explanation and not by way of limitation.

EXAMPLES

In the following examples, coconut fatty acid aminoamides, for example, are prepared from different fat raw materials and 3-N,N-dimethylaminopropylamine, as well as from sodium monochloroacetate of conventional commercial quality.

In Examples A1 to A4, betaine solutions are prepared, which are not of the invention. In Examples A1 and A2, the acid number is adjusted to a value which lies outside of the required range, while in the inventive Examples B1 to B3, which otherwise are similar, liquid betaine solutions with 45% solids are obtained. No glycerin is contained in Example A3, although this would have been necessary in order to achieve a flowable product. This is shown by the otherwise similar inventive Example B4. In Example A4, which is not of the invention, the pH has not been adjusted to a value from 5 to 8.

The fatty acid aminoamides used are characterized by:

| Fatty Acid Aminoamide A: | |
| --- | --- |
| tertiary amine nitrogen content: | 4.6% |
| acid number: | 2.1 |
| glycerin content: | 3.0% |
| fatty acid distribution: | |

-continued

| | |
|---|---|
| caproic | 0.5% |
| caprylic | 6.7% |
| capric | 6.5% |
| lauric | 48.0% |
| myristic | 17.5% |
| palmitic | 12.0% |
| stearic | 8.9% |
| oleic | — |
| linoleic | — |
| Fatty Acid Aminoamide B: | |
| tertiary amine nitrogen content: | 4.3% |
| acid number: | 4.1 |
| glycerin content: | — |
| fatty acid distribution: | |
| caproic | 1.0% |
| caprylic | 7.0% |
| capric | 6.0% |
| lauric | 48.0% |
| myristic | 19.0% |
| palmitic | 9.0% |
| stearic | 10.0% |
| oleic | — |
| linoleic | — |
| Fatty Acid Aminoamide C: | |
| tertiary amine nitrogen content: | 4.42% |
| acid number: | 4.3 |
| glycerin content: | — |
| fatty acid distribution: | |
| caproic | 1.0% |
| caprylic | 7.0% |
| capric | 6.0% |
| lauric | 48.0% |
| myristic | 19.0% |
| palmitic | 9.0% |
| stearic | 2.0% |
| oleic | 7.0% |
| linoleic | 1.0% |
| Fatty Acid Aminoamide D: | |
| tertiary amine nitrogen content: | 4.2% |
| acid number: | 2.1 |
| glycerin content: | 2.9% |
| fatty acid distribution: | |
| caproic | — |
| caprylic | 7.0% |
| capric | 6.0% |
| lauric | 48.0% |
| myristic | 17.0% |
| palmitic | 7.0% |
| stearic | 3.0% |
| oleic | 11.0% |
| linoleic | 1.0% |
| Fatty Acid Aminoamide E: | |
| tertiary amine nitrogen content: | 4.2% |
| acid number: | 1.8 |
| glycerin content: | 3.3% |
| fatty acid distribution: | |
| caproic | — |
| caprylic | 3.0% |
| capric | 3.0% |
| lauric | 50.0% |
| myristic | 17.0% |
| palmitic | 12.0% |
| stearic | 5.0% |
| oleic | 10.0% |
| linoleic | — |
| Fatty Acid Aminoamide F: | |
| tertiary amine nitrogen content: | 4.42% |
| acid number: | 4.3 |
| glycerin content: | 2.9% |
| fatty acid distribution: | |
| caproic | 1.0% |
| caprylic | 7.0% |
| capric | 12.0% |
| lauric | 40.0% |
| myristic | 19.0% |
| palmitic | 12.0% |
| stearic | 9.0% |
| oleic | — |
| linoleic | — |

-continued

| | |
|---|---|
| Fatty Acid Aminoamide G: | |
| tertiary amine nitrogen content: | 4.6% |
| acid number: | 18 |
| glycerin content: | — |
| fatty acid distribution: | |
| caproic | 1.0% |
| caprylic | 7.0% |
| capric | 6.0% |
| lauric | 48.0% |
| myristic | 19.0% |
| palmitic | 9.0% |
| stearic | 2.0% |
| oleic | 7.0% |
| linoleic | 1.0% |

A) EXAMPLES NOT OF THE INVENTION

Example A1

Coconut fatty acid aminoamide A (305 g) is mixed with 1.1 g of coconut fatty acids having an acid number of 290. The resulting mixture of coconut fatty acid aminoamide and fatty acids has an acid number of 3; this corresponds to 0.36% fatty acids, calculated as lauric acid. The mixture is added to a solution of 131 g of 98% sodium monochloroacetate (1.1 moles) in 534 g of water and heated with stirring to 98° C- The pH during the reaction is maintained at a value between 8 and 9 by the addition of a few drops (approximately 1.5 mL) of 40% NaOH. The reaction is stopped after 8 hours. Before the temperature is lowered, the pH is adjusted to a value of 6 with aqueous hydrochloric acid. A gel-like, nonflowable product is formed, which is characterized by the following values:

Solids: 45%
Betaine: 37.2%
NaCl: 6.7%
Fatty acids: 0.1%
Glycerin: 0.97%
Aminoamide: <0.3%
pH: 6.0

Example A2

Coconut fatty acid aminoamide A (305 g) is mixed with 39 g coconut fatty acids having an acid number of 290. The resulting mixture of coconut fatty acid aminoamide and fatty acids has an acid number of 35; this corresponds to 11.3% fatty acids, calculated as lauric acid. The mixture is added to a solution of 131 g of 98% sodium monochloroacetate (1.1 moles) in 581 g of water and heated with stirring to 98° C. The pH of the reaction is maintained between 8 and 9 by the addition of a few drops (approximately 1.5 mL) of 40% NaOH. During the reaction, the viscosity increases greatly and the reaction mixture can be stirred only with difficulty. The reaction is stopped after 8 hours. Before the temperature is lowered, the pH is adjusted to a value of 6 with 10% aqueous hydrochloric acid. A cloudy, viscous, pasty, nonflowable product is formed, which is characterized by the following values:

Solids: 45%
Betaine: 34.1%
NaCl: 6.2%
Fatty acids: 3.8%
Glycerin: 0.98%
Aminoamide: 0.5%
pH: 6.0

Example A3

Coconut fatty acid aminoamide B (326 g) is mixed with 16.7 g of lauric acid having an acid number of 290. The resulting mixture of coconut fatty acid aminoamide and fatty acids has an acid number of 18; this corresponds to 4.9% fatty acids, calculated as lauric acid. The mixture is added to a solution of 131 g (1.1 moles) of 98% sodium monochloroacetate in 575 g of water and heated with stirring to 98° C. The pH of the reaction is maintained between 8 and 9 by the addition of a few drops (approximately 1.5 mL) of 40% NaOH. The reaction is stopped after 8 hours. Before the temperature is lowered, the pH is adjusted to a value of 6 with 10% hydrochloric acid. A gelatinous, non-flowable product is formed, which is characterized by the following values:

Solids: 45%
Betaine: 36.7%
NaCl: 6.2%
Fatty acids: 1.56%
Glycerin: —
Aminoamide: <0.3%
pH: 6.0

Example A4

Coconut fatty acid aminoamide A (305 g) is mixed with 17.5 g of lauric acid having an acid number of 290. The resulting mixture of coconut fatty acid aminoamide and fatty acids has an acid number of 18; this corresponds to 5.4% fatty acids, calculated as lauric acid. The mixture is added to a solution of 131 g of 98% sodium monochloroacetate (1.1 moles) in 554 g of water and heated with stirring to 120° C. The pH of the reaction is maintained between 8 and 9 by the addition of a few drops (approximately 1.5 mL) of 40% NaOH. The reaction is stopped after 8 hours. Subsequently, the pH is not changed by the addition of acid. A clear, solid product is formed, which is characterized by the following values:

Solids: 45%
Betaine: 35.2%
NaCl: 6.5%
Fatty acids: 1.78%
Glycerin: 1.0%
Aminoamide: <0.3%
pH: 8.6

B) EXAMPLES OF THE INVENTION

Example B1

Coconut fatty acid aminoamide A (305 g) is mixed with 11 g of coconut fatty acids having an acid number of 290. The resulting mixture of coconut fatty acid aminoamide and fatty acids has an acid number of 12; this corresponds to 3.8% fatty acids, calculated as lauric acid. The mixture is added to a solution of 131 g of 98% sodium monochloroacetate (1.1 moles) in 546 g of water and heated with stirring to 98° C. The pH of the reaction is maintained between 8 and 9 by the addition of a few drops (approximately 1.5 mL) of 40% NaOH. The reaction is stopped after 8 hours. Before the temperature is lowered, the pH is adjusted to a value of 5.5 with hydrochloric acid. A clear, liquid product is formed, which is characterized by the following values:

Solids: 45%
Betaine: 36%
NaCl: 6.6%
Fatty acids: 1.1%
Glycerin: 0.94%
Aminoamide: <0.3%
pH: 5.5
Viscosity: 90 mPas

Example B2

Coconut fatty acid aminoamide A (305 g) is mixed with 17.5 g of coconut fatty acids having an acid number of 290. The resulting mixture of coconut fatty acid aminoamide and fatty acids has an acid number of 18; this corresponds to 5.7% fatty acids, calculated as lauric acid. The mixture is added to a solution of 131 g of 98% sodium monochloroacetate (1.1 moles) in 554 g of water and heated with stirring to 98° C. The pH of the reaction is maintained between 8 and 9 by the addition of a few drops (approximately 1.5 mL) of 40% NaOH. The reaction is stopped after 8 hours. Before the temperature is lowered, the pH is adjusted to a value of 5 with 10% aqueous hydrochloric acid. A clear, liquid product is formed, which is characterized by the following values:

Solids: 45%
Betaine: 35.8%
NaCl: 6.5%
Fatty acids: 1.8%
Glycerin: 0.93%
Aminoamide: <0.3%
pH: 5.0
Viscosity: 90 mPas

Example B3

Coconut fatty acid aminoamide A (305 g) is mixed with 29 g of coconut fatty acids having an acid number of 290. The resulting mixture of coconut fatty acid aminoamide and fatty acids has an acid number of 27; this corresponds to 8.7% fatty acids, calculated as lauric acid. The mixture is added to a solution of 131 g of 98% sodium monochloroacetate (1.1 moles) in 568 g of water and heated with stirring to 98° C. The pH of the reaction is maintained between 8 and 9 by the addition of a few drops (approximately 1.5 mL) of 40% NaOH. The reaction is stopped after 8 hours. Before the temperature is lowered, the pH is adjusted to a value of 6 with aqueous hydrochloric acid. A clear, liquid product is formed, which is characterized by the following values:

Solids: 45%
Betaine: 34.5%
NaCl: 6.3%
Fatty acids: 2.9%
Glycerin: 0.9%
Aminoamide: <0.3%
pH: 6.0
Viscosity: 110 mPas

Example B4

Coconut fatty acid aminoamide B (326 g) is mixed with 17.5 g of coconut fatty acids having an acid number of 290 and 10.6 g of glycerin. The resulting mixture of coconut fatty acid aminoamide and fatty acids and glycerin has an acid number of 18, corresponding to 5.4% fatty acids, calculated as lauric acid, and a glycerin content of 3%. The mixture is added to a solution of 131 g of 98% sodium monochloroacetate (1.1 moles) in 593 g of water and heated with stirring to 98° C. The reaction is stopped after 8 hours. A clear, liquid product is formed, which is characterized by the following values:

Solids: 45%
Betaine: 35.5%
NaCl: 6.1%
Fatty acids: 1.78%
Glycerin: 0.93%
Aminoamide: 0.7%
pH: 5.5
Viscosity: 85 mPas

Example B5

Coconut fatty acid aminoamide A (305 g) is mixed with 17.5 g of lauric acid having an acid number of 290. The resulting mixture of coconut fatty acid aminoamide and fatty acids has an acid number of 18; this corresponds to 5.4% fatty acids, calculated as lauric acid. The mixture is added to a solution of 143 g of 98% sodium monochloroacetate (1.2 moles) in 569 g of water and heated with stirring in an autoclave to 140° C., the pressure increasing to 3.5 bar. It is advantageous to carry out the reaction at an elevated temperature, because the viscosity of the reaction medium is lowered and the reaction time is shortened at such a temperature. The reaction is stopped after 4 hours. A clear, liquid product is formed, which is characterized by the following values:
Solids: 45%
Betaine: 34.6%
NaCl: 6.9%
Fatty acids: 1.78%
Glycerin: 0.93%
Aminoamide: 0.5%
pH: 5.3
Viscosity: 90 mPas

Example B6

Coconut fatty acid aminoamide C (317 g) is mixed with 17.1 g of not hydrogenated coconut fatty acids having an acid number of 278. The resulting mixture of coconut fatty acid aminoamide and fatty acids has an acid number of 18, which corresponds to 5.2 fatty acids, calculated as lauric acid. The mixture is added to a solution of 131 g of 98% sodium monochloroacetate (1.1 moles) in 504 g of water and heated with stirring to 98° C. The pH of the reaction is maintained between 8 and 9 by the addition of a few drops (approximately 1.5 mL) of 40% NaOH. The reaction is stopped after 8 hours. Before the temperature is lowered, the pH is adjusted to a value of 5.5 with a few drops of hydrochloric acid. A clear, liquid product is formed, which is characterized by the following values:
Solids: 48%
Betaine: 39%
NaCl: 6.7%
Fatty acids: 1.8%
Glycerin: —
Aminoamide: 0.5%
pH: 5.5
Viscosity: 120 mPas

Example B7

Coconut fatty acid aminoamide D (333 g) is mixed with 11 g lauric acid having an acid number of 290. The resulting mixture of coconut fatty acid aminoamide and fatty acids has an acid number of 12, which corresponds to 3.2% fatty acids, calculated as lauric acid. The mixture is added to a solution of 131 g of 98% sodium monochloroacetate (1.1 moles) in 581 g of water and heated with stirring to 98° C. The pH of the reaction is maintained between 8 and 9 by the addition of a few drops (approximately 1.5 mL) of 40% NaOH. The reaction is stopped after 8 hours. Before the temperature is lowered, the pH is adjusted to a value of 7.5 with a few drops of 10% hydrochloric acid. A clear, liquid product is formed, which is characterized by the following values:
Solids: 45%
Betaine: 36.8%
NaCl: 6.2%
Fatty acids: 1.06%
Glycerin: 0.89%
Aminoamide: <0.3%
pH: 7.5
Viscosity: 75 mPas

Example B8

Coconut fatty acid aminoamide B (326 g) is mixed with 10.9 g of glycerin; this corresponds to a glycerin content of 3.2%. The mixture is added to a solution of 131 g of 98% sodium monochloroacetate (1.1 moles) in 646 g of water and heated with stirring to 98° C. The pH of the reaction is maintained between 8 and 9 by the addition of a few drops (approximately 1.5 mL) of 40% NaOH. The reaction is stopped after 8 hours. Before the temperature is lowered, the pH is adjusted to a value of 7 with a few drops of 10% hydrochloric acid. A clear, liquid product is formed, which is characterized by the following values:
Solids: 42%
Betaine: 33.3%
NaCl: 5.9%
Fatty acids: 1.8%
Glycerin: 1.0%
Aminoamide: <0.3%
pH: 7.0
Viscosity: 75 mPas

Example B9

Coconut fatty acid aminoamide E (317 g) is mixed with 24.3 g of oleic acid with an acid number of 200. The resulting mixture of fatty acid aminoamide and fatty acid has an acid number of 18; this corresponds to 7.1% fatty acids, calculated as lauric acid. The mixture is added to a solution of 131 g of 98% sodium monochloroacetate (1.1 moles) in 577 g of water and heated with stirring to 98° C. The reaction is stopped after 8 hours. The product has a pH of 7.5. A liquid product is formed, which is characterized by the following values:
Solids: 45%
Betaine: 36.7%
NaCl: 6.2%
Fatty acids: 1.78%
Glycerin: —
Aminoamide: 0.3%
pH: 7.5
Viscosity: 90 mPas

Example B10

Coconut fatty acid aminoamide F (316 g) is mixed with 16.5 g of lauric acid with an acid number of 290. The resulting mixture of fatty acid aminoamide and fatty acids has an acid number of 18; this corresponds to 5.4% fatty acids, calculated as lauric acid. The mixture is added to a solution of 131 g of 98% sodium monochloroacetate (1.1 moles) in 567 g of water and heated with stirring to 98° C. The pH is maintained during the reaction at a value between 8 and 9 by the addition of a few drops (approximately 1.5mL) of 40% NaOH. The reaction is stopped after 8 hours. Before the temperature is lowered, the pH is adjusted to a value of 5.5 with hydrochloric acid. A clear, liquid product is formed, which is characterized by the following values:
Solids: 45%
Betaine: 36.7%
NaCl: 6.3%
Fatty acids: 1.1%
Glycerin: 0.94%
Aminoamide: <0.3%
pH: 5.5
Viscosity: 85 mPas

Example B11

Coconut fatty acid aminoamide G (329 g) is added to a solution of 131 g of 98% sodium monochloroacetate (1.1 moles) in 562 g of water and heated with stirring to 98° C. The pH is maintained during the reaction at a value between 8 and 9 by the addition of a few drops (approximately 1.5mL) of 40% NaOH. The reaction is stopped after 8 hours. Before the temperature is lowered, the pH is adjusted to a value of 6 with 10% aqueous hydrochloric acid. A clear, liquid product is formed, which is characterized by the following values:
Solids: 45%
Betaine: 36.4%
NaCl: 6.4%
Fatty acids: 1.78%
Glycerin: 0.97%
Aminoamide: 0.4%
pH: 6.0
Viscosity: 95 mPas

C) PRESERVATIVE LOADING TESTS

Example C

The betaine solution, prepared in Example B7, and its aqueous dilutions to 40% and 35% solids are subjected to a microbiological loading test (preservation loading test), according to Karl Heinz Wallhaeusser "Praxis der Sterilisation, Desinfektion, Konservierung, Keimidentifizierung, Betriebshygiene" (The practice of Sterilization, Disinfection, Preservation, Microorganism Identification, Factory Hygiene) 3rd Edition, page 336 ff., published by Georg Thieme, Stuttgart, 1984. Each of these samples (10 mL) was inoculated with approximately 105 microorganisms of the following types:
Staphylococcus aureus
Escherichia coli
Pseudomonas aeruginosa
Candida albicans
Aspergillus niger
Candida lipolytica The germ counts were determined after 1, 24 and 72 hours, as well as after 7 days. The results are summarized in the following Tables.

TABLE 1

| | Betaine Solution with 35% Solids | | | |
|---|---|---|---|---|
| | Germ Count After | | | |
| Test Organism | 1 hour | 24 hours | 72 hours | 7 days |
| Staphylococcus aureus | $1.4 \times 10^3$ | <10 | <10 | <10 |
| Escherichia coli | $1.4 \times 10^5$ | $1.5 \times 10^4$ | <10 | <10 |
| Pseudomonas aeruginosa | $2.6 \times 10^4$ | $1.0 \times 10^2$ | $1.0 \times 10^1$ | <10 |
| Candida albicans | $1.0 \times 10^1$ | $1.0 \times 10^1$ | <10 | <10 |
| Aspergillus niger | $2.0 \times 10^5$ | $1.0 \times 10^5$ | $7.0 \times 10^3$ | $2.0 \times 10^3$ |

TABLE 1-continued

| | Betaine Solution with 35% Solids | | | |
|---|---|---|---|---|
| | Germ Count After | | | |
| Test Organism | 1 hour | 24 hours | 72 hours | 7 days |
| Candida lipolytica | $1.1 \times 10^5$ | $2.9 \times 10^4$ | $3.8 \times 10^3$ | $3.9 \times 10^3$ |

TABLE 2

| | Betaine Solution with 35% Solids | | | |
|---|---|---|---|---|
| | Germ Count After | | | |
| Test Organism | 1 hour | 24 hours | 72 hours | 7 days |
| Staphylococcus aureus | $2.7 \times 10^3$ | <10 | <10 | <10 |
| Escherichia coli | $4.9 \times 10^4$ | $2.3 \times 10^3$ | <10 | <10 |
| Pseudomonas aeruginosa | $1.3 \times 10^4$ | $3.0 \times 10^2$ | <10 | <10 |
| Candida albicans | $1.0 \times 10^1$ | <10 | <10 | <10 |
| Aspergillus niger | $1.7 \times 10^5$ | $1.2 \times 10^5$ | $1.2 \times 10^3$ | $1.0 \times 10^2$ |
| Candida lipolytica | $1.2 \times 10^5$ | $2.2 \times 10^4$ | $2.0 \times 10^3$ | $5.0 \times 10^1$ |

TABLE 3

| | Betaine Solution with 45% Solids | | | |
|---|---|---|---|---|
| | Germ Count After | | | |
| Test Organism | 1 hour | 24 hours | 72 hours | 7 days |
| Staphylococcus aureus | $1.0 \times 10^2$ | <10 | <10 | <10 |
| Escherichia coli | $1.0 \times 10^4$ | <10 | <10 | <10 |
| Pseudomonas aeruginosa | $8.0 \times 10^3$ | $4.0 \times 10^1$ | <10 | <10 |
| Candida albicans | <10 | <10 | <10 | <10 |
| Aspergillus niger | $2.3 \times 10^5$ | $1.7 \times 10^5$ | $2.0 \times 10^2$ | $1.0 \times 10^1$ |
| Candida lipolytica | $4.3 \times 10^4$ | $2.2 \times 10^3$ | <10 | <10 |

According to Wallhaeusser, the preservation is adequate "if, within a period of less than three weeks, the inoculated bacteria are reduced to fewer than 100 micro-organisms per mL". This requirement is fulfilled best by the betaine solution with 45% solids. The betaine solution with 40% solids still satisfies the requirement, while the betaine solution with 35% solids does not show adequate resistance to microorganisms.

We claim:

1. An aqueous liquid solution of a betaine of the formula

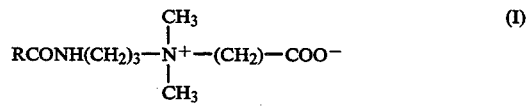

in which R is an alkyl group of coconut fatty acids, hydrogenated coconut fatty acids or a fatty acid mixture which on the average corresponds to coconut fatty acids, wherein the solution has a solids content of at least 40% by weight, a pH of 5 to 8 and an aminoamide content of not more than 1% by weight and comprises 1 to 3% by weight, based on the solution, of one or more saturated fatty acids with an average of 8 to 18 carbon atoms or one or more unsaturated fatty acids with an average of 8 to 24 carbon atoms and 0 to 4% by weight of glycerin, based on the solution, provided said saturated or unsaturated fatty acid is a compound selected from a member of the group consisting of lauric acid, oleic acid, ricinoleic acid, coconut fatty and hydrogenated coconut fatty acid.

2. The betaine solution of claim 1, which comprises 1.5 to 3% by weight of said saturated or unsaturated fatty acids.

3. The betaine solution of claim 1, which contains a compound of the formula RCOOH as said saturated or unsaturated fatty acid, wherein R has the meaning already given.

4. The betaine solution of claim 2, which contains a compound of the formula RCOOH as said saturated or unsaturated fatty acid, wherein R has the meaning already given.

5. The betaine solution of claim 2, which contains as said saturated or unsaturated fatty acid a compound selected from a member of the group consisting of lauric acid, oleic acid, ricinoleic acid, coconut fatty acid and hydrogenated coconut fatty acid.

6. The betaine solution of claim I which comprises 1 to 2% by weight of glycerin.

7. The betaine solution of claim 2 which comprises 1 to 2% by weight of glycerin.

8. The betaine solution of claim 3 which comprises 1 to 2% by weight of glycerin.

9. The betaine solution of claim 4 which comprises 1 to 2% by weight of glycerin.

10. A method for the preparation of a betaine solution of claim 1 comprising quaternizing a compound of the formula $$RCONH(CH_2)_3-N-(CH_3)_2 \qquad (II)$$

where R is an alkyl group of coconut fatty acids, hydrogenated coconut fatty acids or a fatty acid mixture which, on average, corresponds to coconut fatty acids, with chloroacetic acid or a salt thereof at elevated temperature, for the quaternization reaction, wherein a fatty acid amino amide of the formula II is used which contains the required amount of said saturated or unsaturated fatty acid as free fatty acid, or the required amount of said saturated or unsaturated fatty acid is added to the reaction mixture before or during the quaternization reaction and optionally, glycerin is added to the reaction mixture, further provided that said saturated or unsaturated fatty acid is a compound selected from a member of the group consisting of lauric acid, oleic acid, ricinoleic acid, coconut fatty acid or hydrogenated coconut fatty acid.

* * * * *